United States Patent [19] [11] Patent Number: 5,464,925
Moyer et al. [45] Date of Patent: Nov. 7, 1995

[54] BENZOCYCLOBUTENE-TERMINATED POLYMIDES

[75] Inventors: Eric S. Moyer; Denise J. D. Moyer, both of Midland, Mich.

[73] Assignee: The Dow Chemical Company, Midland, Mich.

[21] Appl. No.: 248,906

[22] Filed: May 25, 1994

[51] Int. Cl.$^6$ .................................................... C08G 73/10
[52] U.S. Cl. ..................... 528/170; 528/172; 528/173; 528/174; 528/185; 528/188; 528/200; 528/229; 528/321; 528/322; 528/350; 528/353
[58] Field of Search ...................................... 528/170, 220, 528/185, 321, 188, 322, 172, 173, 174, 229, 353, 350

[56] References Cited

U.S. PATENT DOCUMENTS 4,540,763  9/1985  Kirchhoff .
4,696,994  9/1987  Nakajima et al. .
4,711,964  12/1987  Tan et al. .

FOREIGN PATENT DOCUMENTS

0418406A1  3/1991  European Pat. Off. .

*Primary Examiner*—Paul R. Michl
*Assistant Examiner*—P. Hampton-Hightower

[57] ABSTRACT

The present invention is an oligomer represented by the formula:

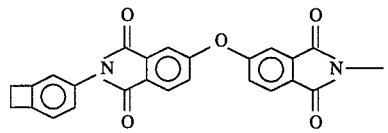

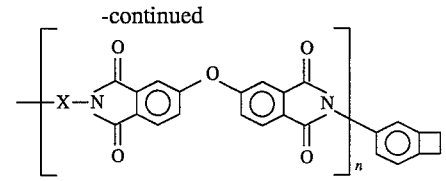

wherein X is a moiety selected from the group consisting of:

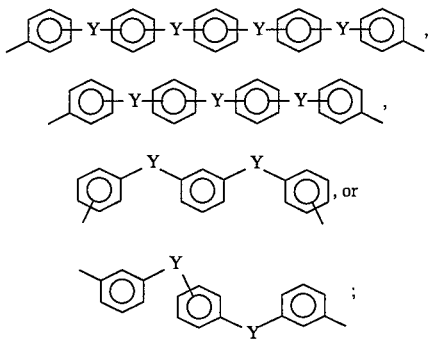

where each Y is independently S, O, $CH_2$, C=O, $CH_3$—C—$CH_3$, O=S=O, or $CF_3$—C—$CF_3$.

In another aspect, the present invention is a polymer of the above-described oligomer.

The benzocyclobutene-terminated polyimides of the present invention can be cured to form novel polymers that exhibit high adhesive strength. The preferred benzocyclobutene-terminated polyimides of the present invention are more highly processable than conventional polyimide systems, yet form polymers that are thermally stable at temperatures above 200° C.

11 Claims, No Drawings

BENZOCYCLOBUTENE-TERMINATED POLYIMIDES

BACKGROUND OF INVENTION

This invention relates to a class of benzocyclobutene-terminated polyimide oligomers that are useful for high performance adhesive applications.

Because adhesives are lighter and more resistant to fatigue than mechanical fasteners, adhesive bonding of metallic and composite structures has become the preferred choice for military aircraft and aerospace applications. One concern about adhesively bonded joints is long-term stability. Metal-adhesive joints tend to degrade upon exposure to severe environments, particularly the high temperatures and humidities encountered in aircraft and aerospace applications.

Much effort has been directed toward the preparation of adhesives that exhibit high strength, good mechanical properties, and thermostability at temperatures above 200° C. Epoxy adhesives are known to perform satisfactorily for over 15,000 hours at 150° C., but only for short periods at 200° C. For example, Adams teaches that epoxy phenolics, a mixture of epoxy and phenolic resins, degrade over a long period of time at 160° C. (See R. D. Adams, "Adhesives for High-Temperature Applications", European Conf. on High Temperature Materials in Engineering Metals, Ceramics, Plastics, Apr. 27–28, 1989.)

Polyimides have also been targeted for high performance adhesive applications, primarily for their high thermostability. Unfortunately, they tend to be intractable in their fully imidized form, making processing difficult. To address this processing problem, flexibilizing groups such as fluoroalkylene units (J. P. Critchley et al, J. Poly Science, vol. 10, page 1809, (1972)), or bulky side groups (Harris et al. in "Polyimides: Synthesis, Characterization and Applications", K. L. Mittal, ed. Plenum, New York, volume 1, page 3, (1984)) or asymmetric catenates (Burks et al. in "Polyimides: Synthesis, Characterization and Applications", supra, page 119) have been incorporated into the polymer backbone to achieve tractable, processable polyimides. However, this improvement in processability is offset by the undesirable decrease in solvent resistance as well as glass transition temperature. Polyimides also require a curing step, during which volatiles are released. This is particularly a problem when curing large-area metal-to-metal surfaces, where volatiles can be trapped and cause voids in the bonded joint. (See Millard in "Adhesive Bonding of Al Alloys", E. W. Thrall and R. W. Shannon, eds., volume 8, Marcel Dekker, Inc., New York, pages 129 and 133, 1985.)

One way to solve the problem of volatile release upon curing is to endcap already cyclized imides with benzocyclobutene (BCB) prior to a curing step. Then, upon curing, the BCB polymerizes without releasing volatiles. Kirchhoff (U.S. Pat. No. 4,540,763, incorporated herein by reference) discloses bisbenzocyclobutenes and polymers derived therefrom. The bisbenzocyclobutene moieties are connected by a direct bond or through a bridging group, such as a cyclic imido group. Tan and Arnold (U.S. Pat. No. 4,711,964, incorporated herein by reference) discloses the synthesis of bisbenzocyclobutene imide compounds, the polymers of which form high temperature-resistant thermoset resins that are useful in composite materials in advanced aircraft and aerospace vehicles.

What remains elusive is a BCB endcapped imide oligomer which 1) has a glass transition temperature, $T_g$, that is lower than the temperature at which polymerization of the BCB moieties proceeds rapidly; 2) forms a polymer that is thermally stable above 200° C.; 3) does not release volatiles upon curing and; 4) has adhesive properties that are acceptable for high performance applications.

SUMMARY OF INVENTION

The present invention is an oligomer represented by the formula:

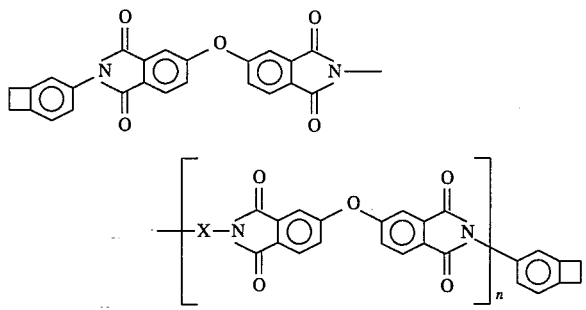

wherein X is:

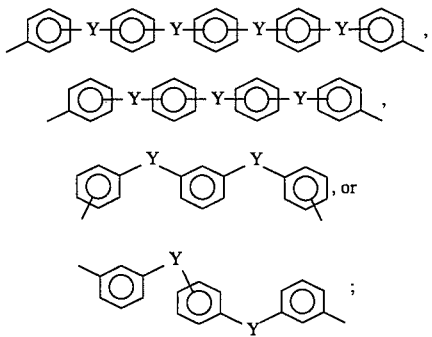

where each Y is independently S, O, $CH_2$, C=O, $CH_3$—C—$CH_3$, O=S=O, or $CF_3$—C—$CF_3$.

In another aspect, the present invention is a polymer of the above-described oligomer.

The benzocyclobutene-terminated polyimides of the present invention can be cured to form novel polymers that exhibit high adhesive strength. The preferred benzocyclobutene-terminated polyimides of the present invention are more highly processable than conventional polyimide systems, yet form polymers that are thermally stable at temperatures above 200° C. Thus, these compounds represent an advance in the art of high performance adhesives.

DETAILED DESCRIPTION OF INVENTION

The oligomers of the present invention can be prepared in two steps by first reacting a bisaniline together with 4,4'-oxydiphthalic anhydride (ODPA), and 4-amino-benzocyclobutene (4-amino-BCB) in an inert atmosphere, such as nitrogen. The reaction is preferably carried out at approximately room temperature in the presence of a polar aprotic solvent, such as N-methyl pyrrolidinone, to form a poly(amic acid). The bisaniline is of the form $NH_2$—X—$NH_2$, where X is a moiety selected from the group consisting of:

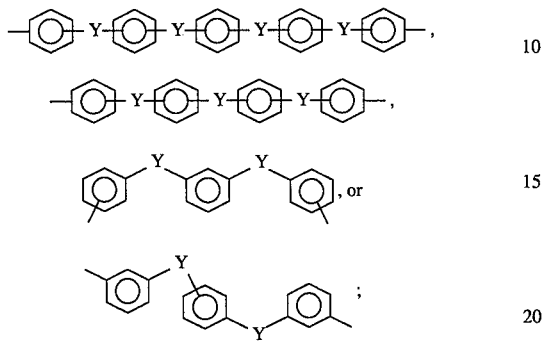

where each Y is independently S, O, $CH_2$, C=O, $CH_3$—C—$CH_3$, O=S=O, or $CF_3$—C—$CF_3$.

It is to be understood that when a Y group is shown to be attached to a benzene ring between 2 carbon atoms, the Y group can suitably be attached to either one of the adjacent carbon atoms.

Preferably, X is moiety selected from the group consisting of:

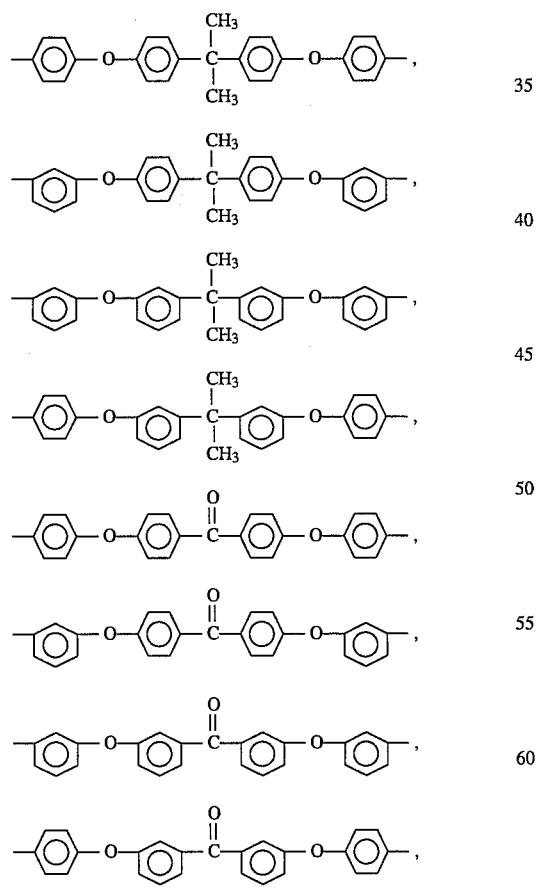

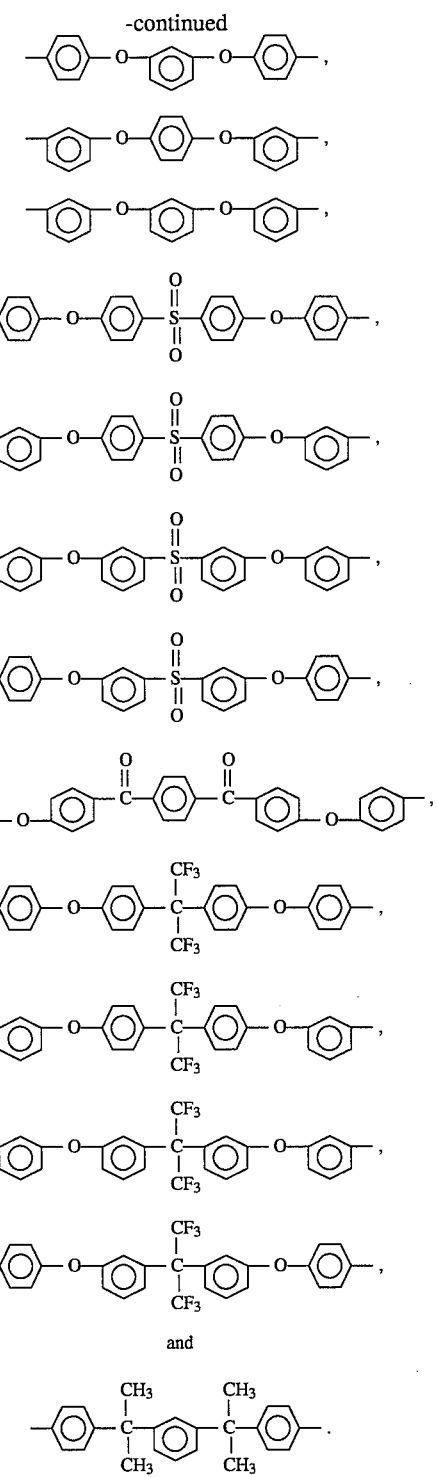

and

More preferably, X is a moiety selected from the group consisting of:

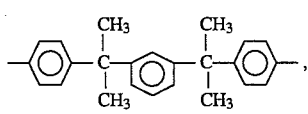

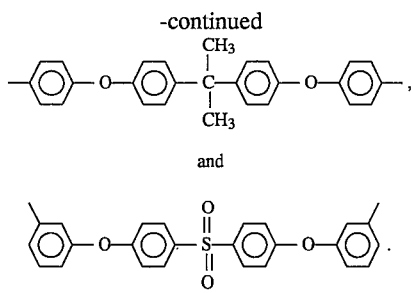

and

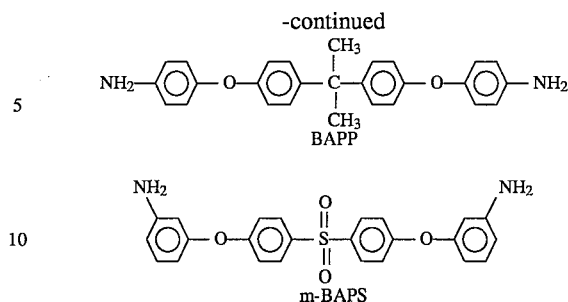

BAPP m-BAPS

The more preferred bisanilines are 4,4'-[1,3-phenylene-(1-methyl ethylidene)]bisaniline (Bis-M), 2,2-bis-(4-[4-aminophenoxy]phenyl)propane (BAPP), or 2,2-bis-(4-[3-aminophenoxy]phenyl)sulfone (m-BAPS). The chemical formulae of these preferred bisanilines are illustrated below:

In the second step, the poly(amic acid) can be cyclodehydrated, preferably in the presence of a polar aprotic solvent that allows water that is released in the course of the reaction to be distilled without substantially distilling the polar aprotic solvent. A combination of N-methyl pyrrolidinone and cyclohexylpyrrolidinone is a suitable solvent for such purpose. The cyclodehydration reaction is carried out at a sufficiently high temperature to promote cyclodehydration-imidization, yet sufficiently low to inhibit the ring opening of the benzocyclobutene moiety, preferably in the range of about 150° C. to about 170° C. The two steps of the reaction are shown below:

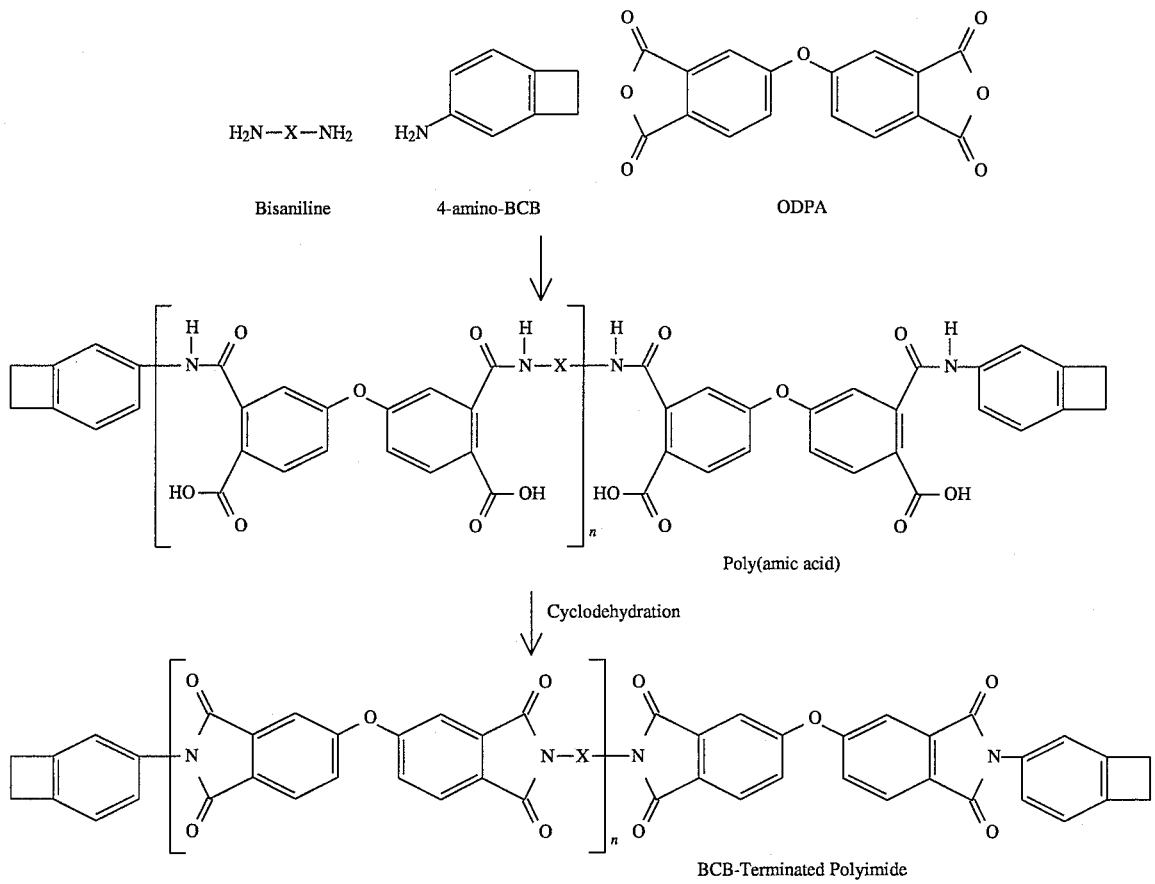

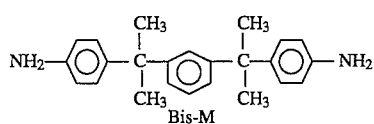

Bis-M

Alternatively, the bisaniline and ODPA can be reacted together in an inert atmosphere, at about room temperature, and in the presence of a polar aprotic solvent to form a bridged dianhydride, which is then reacted with the 4-amino-BCB, preferably under conditions described hereinbefore to form the desired oligomer.

The product BCB-terminated polyimide oligomer has a degree of polymerization (n) of about 1 to about 15, preferably about 1 to about 3, more preferably about to about 2, and most preferably about 1.

The degree of polymerization (n) of the oligomer can be controlled by controlling the amounts of ODPA and bisaniline according to the equation: $n=1/(r-1)$, where r is the mole ratio of ODPA to bisaniline. The amount of 4-amino-BCB used depends on whether it is introduced into the mixture at about the same time as the ODPA and bisaniline, or after the coupled ODPA-bisaniline is formed. When the 4-amino-BCB, ODPA, and bisaniline are all introduced into the reaction vessel at about the same time, 4-amino-BCB is used in sufficiently high quantities to endcap the ODPA-bisaniline moiety (the oligomer without the BCB endcapping), but in sufficiently low quantities to substantially avoid premature reaction with the ODPA. Preferably, the amount of 4-amino-BCB used is about twice the difference between the moles of ODPA and bisaniline used, i.e. BCB=2× (ODPA-bisaniline). However, where the 4-amino-BCB is added after the coupled ODPA-bisaniline is formed, the amount of 4-amino-BCB is not as critical, though a small excess of the 4-amino-BCB is preferable.

The ratio (r) is such that n ranges from about 1 to about 15; preferably from about 1 to about 3; more preferably from about 1 to about 2; and most preferably about 1. Thus, the mole ratio of ODPA to bisaniline ranges from about 2:1 to about 16:15; preferably from about 2:1 to about 4:3; more preferably from about 2:1 to about 3:2; and most preferably about 2:1. Sufficient 4-amino-BCB is used to form endcapped phthalimide groups.

It is desirable that the glass transition temperature ($T_g$) of the the oligomer be lower than the temperature at which polymerization of the BCB moieties proceeds rapidly, so that the oligomer can be easily processed. The $T_g$ of the oligomer is preferably less than 190° C., more preferably less than 180° C., and most preferably less than 170° C. It is further desirable that the $T_g$ of the polymer be as high as possible. In general, the lower the degree of polymerization, the lower the $T_g$ of the oligomer and the higher the $T_g$ of the polymer derived therefrom. It is for these reasons that oligomers with low degrees of polymerization are preferred.

Example 1 shows that the $T_g$s of BCB-endcapped ODPA/BAPP and ODPA/Bis-M oligomers having an n of 1 exhibit lower $T_g$s than the oligomers with an n of 6 and, furthermore, that the polymers derived from the oligomers with n of 1 exhibit higher $T_g$s than the polymers derived from oligomers with n of 6.

EXAMPLE 1

The $T_g$s of BCB-Endcapped Polyimides

| Degree of Polymerization (n) | Oligomer $T_g$ (°C.) | Polymer $T_g$ (°C.) |
| --- | --- | --- |
| ODPA/BAPP/BCB (1) | 174 | 304 |
| ODPA/BAPP/BCB (6) | 198 | 247 |
| ODPA/BIS-M/BCB (1) | 125 | 286 |
| ODPA/BIS-M/BCB (6) | 181 | 223 |

Examples 2–5 describe the preparation of the oligomers tabulated in Example 1, Example 6 describes the preparation of an ODPA/m-BAPs/BCB oligomer with a degree of polymerization of 1, and Example 7 describes the preparation of the polymers derived from the oligomers of Examples 2–6.

EXAMPLE 2

Preparation of a BCB-Terminated ODPA/Bis-M Oligomer with a Degree of Polymerization of 1

To a stirred solution of 4,4'-[1,3-phenylene-(1-methyl ethylidene)]bisaniline (Bis-M, 11.1 g, 0.03 mol) and 4-amino-benzocyclobutene (4-amino-BCB, 7.7 g, 0.06 mol) dissolved in N-methyl pyrrolidinone (NMP, 30 mL) is added solid 4,4'-oxydiphthalic anhydride (ODPA, 20 g, 0.06 mol) and an NMP rinse (40 mL) under an inert atmosphere of nitrogen at room temperature. The solution is stirred for at least 8 hours, whereupon the resultant amic acid oligomer is transferred to one 250-mL, three-necked, round bottom flask equipped with overhead stirring, a Dean-Stark trap, a condenser, and a drying column. Cyclohexylpyrrolidinone (CHP, 23 ml) is added to the round bottom flask and the solution is heated to 165° C. under a nitrogen purge with stirring. Water and some solvent are collected in the Dean-Stark trap during cyclodehydration-imidization. After 12 hours at 165° C., the solution is allowed to cool to room temperature. Upon cooling, the BCB-terminated polyimide oligomer partially precipitates out of solution. The viscous golden yellow BCB-polyimide solution with some solid precipitated material is further precipitated in a methanol and water mixture (75/25), and the off-white solid is filtered and dried in a vacuum oven overnight at 100° C.

EXAMPLE 3

Preparation of a BCB-Terminated ODPA/Bis-M Oligomer with a Degree of Polymerization of 6

Bis-M (26.87 g, 0.078 mol) and NMP (200 mL) are added to a 1-L, 3-neck, round bottom flask equipped with a condenser, a drying column, and a Dean-Stark trap. The mixture is stirred under nitrogen at room temperature until the Bis-M dissolves. ODPA (28.23 g, 0.091 mol) is added along with 100 mL of NMP, and the mixture is stirred at room temperature for 7 hours. 4-Amino-BCB (3.10 g, 0.026 mol) is added to the mixture and stirring is continued at room temperature for another 16 hours. CHP (75 mL) is then added to the mixture and the solution is heated to 165° C. under nitrogen for 12 hours, and water and some solvent are collected in the Dean-Stark trap. The solution is allowed to cool and the work-up is carried out as described in Example 2.

EXAMPLE 4

Preparation of a BCB-Terminated ODPA/BAPP Oligomer with a Degree of Polymerization of 1

2,2-Bis-(4-[4-aminophenoxy]phenyl)propane (BAPP, 19.42 g, 0.047 mol) and NMP (100 mL) are added to a 1-L, 3-neck, round bottom flask equipped with a condenser, a drying column, and a Dean-Stark trap. The mixture is stirred under nitrogen at room temperature until the BAPP dissolves. ODPA (28.23 g, 0.091 mol) is added along with 100 mL of NMP, and the mixture is stirred at room temperature for 5 hours. 4-Amino-BCB (11.27 g, 0.095 mol) is added to the mixture along with 40 mL of NMP. The reaction is otherwise carried out as described in Example 2.

EXAMPLE 5

Preparation of a BCB-Terminated ODPA/BAPP Oligomer with a Degree of Polymerization of 6

The preparation is carried out as described in Example 4, except that 19.21 g (0.047 mol) of BAPP and 16.94 g (0.055 mol) of ODPA are used.

EXAMPLE 6

Preparation of a BCB-Terminated ODPA/m-BAPS Oligomer with a Degree of Polymerization of 1

ODPA (31.21 g, 0.101 mol), m-BAPs (21.75 g, 0.050 mol) and NMP (220 mL) are added to a 1-L, 3-neck, round bottom flask equipped with a condenser, a drying column, and a Dean-Stark trap. The mixture is stirred under nitrogen at room temperature for 6.5 hours. 4-Amino-BCB (11.99 g, 0.101 mol) is added to the mixture along with 40 mL of NMP. The reaction is otherwise carried out as described in Example 2.

EXAMPLE 7

Preparation of the Polymers Derived from the Oligomers of Examples 2–5 prepared from the reaction of bis-2,2-(4-phthalic anhydrido) hexafluoropropane, phenylene diamine, and 4-aminobenzocyclobutene, as described in Comparative Example A. The preparation of the Bis-M/ODPA/BCB oligomer with n=2 is described in Example 9, and the preparation of the samples for the single lap shear tests is described in Example 10.

EXAMPLE 8

Single Lap Shear Strengths

| BONDING CONDITIONS | PHENYLENE DIAMINE/ 6FDA/BCB Comp Ex A | BIS-M/ODPA BCB n = 1 Ex 2 | BIS-M/ODPA BCB n = 2 Ex 9 | BIS-M/ODPA BCB n = 6 Ex 3 | BAPP/ODPA BCB n = 1 Ex 4 | BAPP/ODPA BCB n = 6 Ex 5 |
|---|---|---|---|---|---|---|
| NEAT 275° C., 1 HR 5 PSI | 624 ± 133 | 3048 ± 397 | 1469 ± 197 | 2396 ± 366 | 1735 ± 200 | 785 ± 101 |
| NEAT 275° C., 1 HR 200 PSI (* = 100 PSI) | 754 ± 158 | 3321 ± 378 | 2151 ± 133 | *3634 ± 401 | 2861 ± 158 | 1538 ± 179 |
| SCRIM 275° C., 1 HR 5 PSI | 219 ± 438 | 3120 ± 231 | 1830 ± 186 | 3076 ± 787 | 2617 ± 611 | 3765 ± 602 |
| SCRIM 275° C., 1 HR 200 PSI (* = 100 PSI) | 1668 ± 158 | 2528 ± 71 | 3041 ± 297 | *5298 ± 573 | 3586 ± 89 | 7096 ± 176 |

The polymers derived from the oligomers of Examples 2–5 are all prepared about the same way. About 5–15 mg of an oligomer are placed in an aluminum DSC pan and sealed. The sample is then placed in a nitrogen purged thermal analyzer and heated from 25° C. to 275° C. at the rate of 10° C./min, then held at 275° C. for 1 hour.

Curing of BCB-terminated Polyimides

The BCB-terminated polyimides of the present invention can be cured to form polymers that are useful as high performance adhesives. These adhesives can be prepared by dissolving the BCB-terminated polyimide in NMP to form a solution that contains from about 10 to about 30 weight percent of the BCB-terminated polyimide. The solution can then be coated onto a finished carrier (solvent coating technique). A woven glass cloth is an example of a carrier used for adhesive tape preparation, and the finish is such that it binds to the surface and has a functional group that can react in a Dieis-Alder fashion with benzocyclobutene upon curing. An example of a suitable finish is 3-methacryloxpropyl trimethoxysilane.

In this solvent coating technique, the solution containing the BCB-terminated polyimide is applied to the carrier until the desired coating thickness (about 0.2 to about 0.3 mm) is obtained. Solvent is removed from the adhesive tape after each coat is applied.

An alternative method of preparing an adhesive tape is melt impregnation, where the neat BCB-terminated polyimide is distributed over the finished carrier, then heated under pressure.

As shown in Example 8, the single lap shear strengths of the adhesives of the present invention are significantly higher (for a variety of bonding conditions) than adhesives formed from 6FDA/phenylene diamine/BCB, a compound described in Tan and Arnold (supra, column 15, Example 6)

Comparative Example A

Preparation of Phenylene Diamine/6FDA/BCB Oligomer with n=1

6FDA, (2,2-bis(3,4-dicarboxyphenyl)hexafluoropropane dianhydride, 27.36 g, 0.062 mol) and NMP (100 mL) are added under nitrogen to a 1-L, 3-neck, round bottom flask equipped with a condenser, a drying column, and a Dean-Stark trap. After the 6FDA dissolves, phenylene diamine (3.33 g, 0.031 mol) is added with 25 mL of NMP and the mixture is stirred for 6 hours. 4-Amino-BCB (7.34 g, 0.62 mol) and NMP (25 mL) are added and the reaction is carried out as described in Example 2.

EXAMPLE 9

Preparation of Bis-M/ODPA/BCB Oligomer with n=2

The reaction is carried out as described in Example 2 except that 0.086 mol (29.63 g) of Bis-M and 0.129 mol (40.02 g) of ODPA and 0.086 mol (10.25 g) 4-amino-BCB are used.

EXAMPLE 10

Preparation of Oligomers for Single Lap Shear Tests

Single lap shear samples are prepared in accordance with A.S.T.M. standard D-1002, wherein either the neat powder or adhesive tape are inserted between Ti 6A1-4V primed adherends using a 0.5-inch overlap.

The oligomer being tested is placed between Ti 6A1-4V primed adherends in a pneumatic press and bonded under four separate sets of conditions: 1) heating the neat powder to 275° C. at 5 psi for 1 hour; 2) heating the neat powder to 275° C. at 200 psi for 1 hour 3) forming a scrim cloth, then heating to 275° C. at 5 psi for 1 hour; and 4) forming a scrim, then heating to 275° C. at 200 psi for 1 hour. The preparation of the Bis-M/ODPA/BCB with n=6 samples are slightly different. Instead of using 200 psi as shown in conditions 2) and 4) the adherends are bonded at 100 psi.

In each case, a bond line film thickness of 0.24 to 0.30 mm is formed. The single lap shear strengths of the samples are measured using a cross head rate of 0.127 cm/min. Lap shear strengths are measured four times and the average and standard deviation are recorded.

Lap Shear Strength as a Function of Temperature

Since the primary requirements of high performance structural adhesives are thermal stability and retention of mechanical properties over a wide temperature range, it is desirable to evaluate lap shear strengths over a broad temperature range. Example 11 shows the average single lap shear strength as a function of temperature, over the temperature range of −54° C. to 288° C., carried out in accordance with A.S.T.M. standard D-1002 for the polymer of Bis-M/ODPA/BCB with n=1 (Example 2). Example 11 also shows that the lap shear strength is actually higher at elevated temperatures than at room temperatures up to at least 232° C., and is also higher at −54° C., than at room temperature. Thus, compounds of the present invention form high performance adhesives that retain thermal stability over a wide temperature range.

EXAMPLE 11

Low and High Temperature Single Lap Shear Strengths for the Polymer of Bis-M/ODPA/BCB with n=1 (Example 2)

| TEST TEMPERATURE (°C.) | AVERAGE SINGLE LAP SHEAR STRENGTH ± ONE STND. DEVIATION (PSI) | PERCENT RETENTION OF ROOM TEMP. STRENGTH |
| --- | --- | --- |
| 22 | 3048 ± 397 | — |
| 177 | 3693 ± 162 | 121 |
| 204 | 3520 ± 109 | 115 |
| 232 | 3183 ± 192 | 104 |
| 260 | 2197 ± 43 | 72 |
| 288 | 1387 ± 172 | 46 |
| −54 | 3616 ± 58 | 119 |

As shown in Example 12, these high performance adhesives can withstand elevated temperatures for extended periods of time. Even when the adhesive system is aged at 204° C. for 5000 hours, 91 to 76 percent of the lap shear strength is retained at temperatures ranging from 177° C. to 232° C. Furthermore, the absolute lap shear strength is still well above the acceptable level of 2000 psi.

EXAMPLE 12

Effect of Isothermal Aging at 204° C. for 1000 and 5000 Hours on Room Temperature and Elevated Temperature Single Lap Shear Strengths for the BCB-Terminated Polyimide, Bis-M/ODPA (Example 2)

| HOURS AGED AT 204° C. | TEST TEMPERATURE (°C.) | AVERAGE SINGLE LAP SHEAR STRENGTH ± ONE STD. DEVIATION (PSI) | PERCENT RETENTION OF ROOM TEMP. STRENGTH |
| --- | --- | --- | --- |
| 1000 | 22 | 2939 ± 127 | 96 |
| 1000 | 177 | 3070 ± 359 | 101 |
| 1000 | 204 | 3202 ± 269 | 105 |
| 1000 | 232 | 2883 ± 211 | 95 |
| 5000 | 22 | 2104 ± 239 | 69 |
| 5000 | 177 | 2767 ± 383 | 91 |
| 5000 | 204 | 2685 ± 512 | 88 |
| 5000 | 232 | 2327 ± 38 | 76 |

The high performance adhesives of the present invention have been shown to withstand exposure to a hot, wet environment. For example, lap shear samples immersed in boiling water for three days and tested at room temperature are found to retain over 80 percent of their strength.

What is claimed is:

1. An oligomer having the formula:

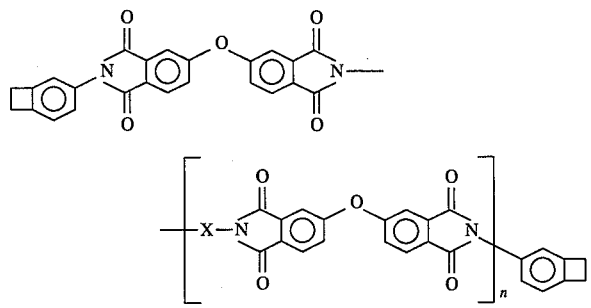

wherein X is:

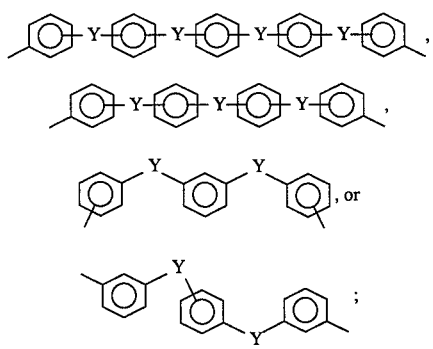

where each Y is independently S, O, $CH_2$, C=O, $CH_3$—C—$CH_3$, O=S=O, or $CF_3$—C—$CF_3$ and n is in the range of about 1 to about 15.

2. The oligomer of claim 1 wherein X is selected from the group consisting of:

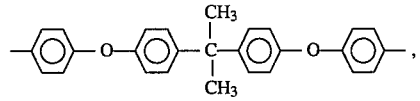

-continued

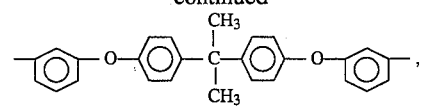
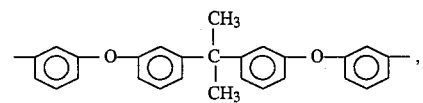
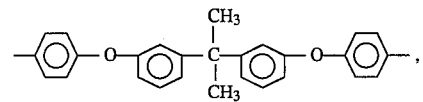
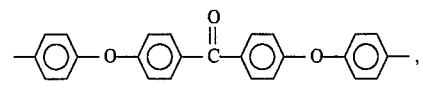
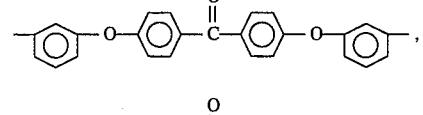
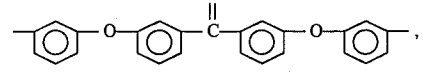
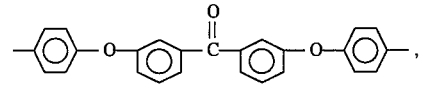
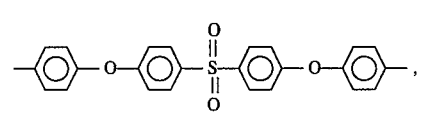
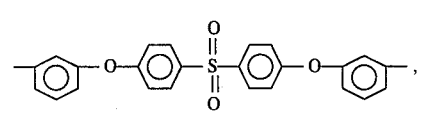
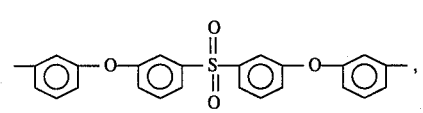
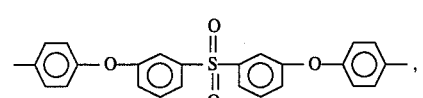
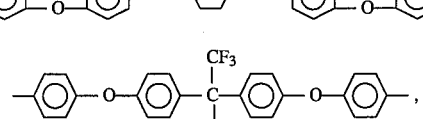

-continued

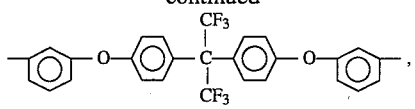
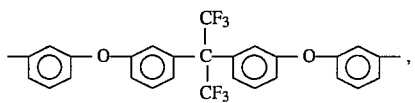
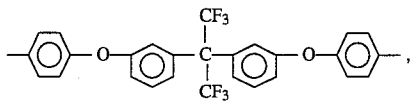

and

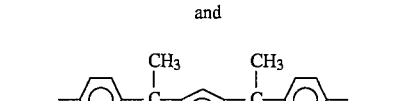

3. The oligomer of claim 2 wherein n is in the range of about 1 to about 6.

4. The oligomer of claim 3 wherein X is selected from the group consisting of:

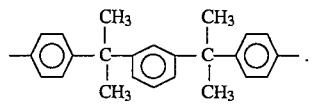
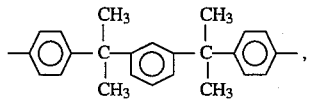

and

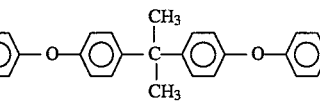

5. The oligomer of claim 4 wherein n is in the range of about 1 to about 2.

6. The oligomer of claim 5 wherein n is about 1.

7. The oligomer of claim 6 wherein X is:

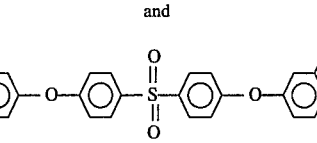

8. A polymer of the oligomer of claim 1.

9. The polymer of claim 8 wherein X is selected from the group consisting of:

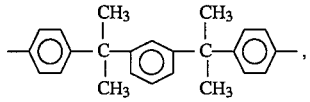
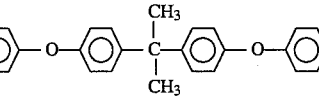

-continued
and
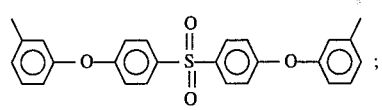
and n is in the range of about 1 to about 6.
10. The polymer of claim 9 wherein n is in the range of about 1 to about 2.
11. The polymer of claim 10 wherein n is about 1.
* * * * *